(12) United States Patent
Lu et al.

(10) Patent No.: US 11,712,149 B2
(45) Date of Patent: Aug. 1, 2023

(54) ENDOSCOPY DEVICES AND METHODS OF USE

(71) Applicant: SUZHOU ACUVU MEDICAL TECHNOLOGY CO. LTD., Suzhou Industrial Park (CN)

(72) Inventors: Fred Lu, Las Vegas, NV (US); Jian Zhang, San Mateo, CA (US); Allen Jiang, Fremont, CA (US)

(73) Assignee: SUZHOU ACUVU MEDICAL TECHNOLOGY CO, LTD., Suzhou Industrial Park (CN)

( * ) Notice: Subject to any disclaimer, the term of this patent is extended or adjusted under 35 U.S.C. 154(b) by 271 days.

(21) Appl. No.: 16/268,909

(22) Filed: Feb. 6, 2019

(65) Prior Publication Data

US 2019/0246873 A1 Aug. 15, 2019

Related U.S. Application Data

(60) Provisional application No. 62/630,718, filed on Feb. 14, 2018.

(51) Int. Cl.
*A61B 1/00* (2006.01)
*A61B 1/05* (2006.01)
(Continued)

(52) U.S. Cl.
CPC ...... *A61B 1/00042* (2022.02); *A61B 1/00009* (2013.01); *A61B 1/00045* (2013.01);
(Continued)

(58) Field of Classification Search
CPC ............ A61B 1/00179; A61B 1/00045; A61B 1/00066; A61B 1/00103; A61B 1/00144;
(Continued)

(56) References Cited

U.S. PATENT DOCUMENTS

| 5,105,269 A | 4/1992 | Nakamura | |
| 5,792,045 A * | 8/1998 | Adair | A61B 1/042 |
| | | | 600/122 |

(Continued)

FOREIGN PATENT DOCUMENTS

| CN | 102028507 | 4/2011 |
| CN | 107638163 | 1/2018 |

(Continued)

OTHER PUBLICATIONS

PCT International Search Report No. PCT/IB2020/000470 dated Nov. 30, 2020.

*Primary Examiner* — Matthew J Kasztejna
(74) *Attorney, Agent, or Firm* — Wissing Miller LLP

(57) ABSTRACT

An endoscopy system that includes a computer system with a high definition display monitor and a handheld portion. The handheld portion includes a re-usable handle portion and a single use portion that is configured to be disposed of following a single use. The single-use portion includes an elongated cannula with an imaging module and illumination modules at its distal tip. The handheld portion includes multiple sensors that can detect and measure rotation of the cannula relative to the handle portion, and rotation of the entire handheld portion. The sensor data is used to correctly orient and display images captured by the imaging module onto the high definition display monitor.

11 Claims, 13 Drawing Sheets

(51) Int. Cl.
  *A61B 1/005* (2006.01)
  *A61B 1/018* (2006.01)
  *A61B 1/06* (2006.01)
  *G02B 23/24* (2006.01)
  *A61B 1/307* (2006.01)

(52) U.S. Cl.
  CPC ........ *A61B 1/0057* (2013.01); *A61B 1/00066* (2013.01); *A61B 1/00103* (2013.01); *A61B 1/00144* (2013.01); *A61B 1/00179* (2013.01); *A61B 1/018* (2013.01); *A61B 1/05* (2013.01); *A61B 1/0676* (2013.01); *A61B 1/307* (2013.01); *G02B 23/2476* (2013.01); *G02B 23/2484* (2013.01); *A61B 1/00096* (2013.01); *G02B 23/2423* (2013.01)

(58) Field of Classification Search
  CPC ......... A61B 1/0057; A61B 1/018; A61B 1/04; A61B 1/00009; A61B 1/0676; A61B 1/307; A61B 1/05; A61B 1/00096; A61B 1/00078; A61B 1/0623; A61B 1/00142; A61B 1/00089; A61B 1/00101; A61B 1/00124; A61B 1/00039; A61B 1/00105; A61B 1/005; A61B 1/00071; G02B 23/2476; G02B 23/2484; G02B 23/2423; G06Q 30/0185
  See application file for complete search history.

(56) References Cited

U.S. PATENT DOCUMENTS

| | | | |
|---|---|---|---|
| 10,448,811 | B2 | 10/2019 | London Brown et al. |
| 2002/0099263 | A1* | 7/2002 | Hale ................. A61B 1/00179 600/117 |
| 2006/0069306 | A1* | 3/2006 | Banik ................. A61B 1/0008 600/118 |
| 2010/0145146 | A1* | 6/2010 | Melder ............. A61B 1/00052 600/112 |
| 2013/0038836 | A1 | 2/2013 | Smith |
| 2015/0112141 | A1* | 4/2015 | Oginski ............ A61B 1/00112 600/136 |
| 2015/0305603 | A1* | 10/2015 | Gal .................... A61B 1/00009 600/103 |
| 2017/0078583 | A1 | 3/2017 | Haggerty |
| 2017/0188795 | A1* | 7/2017 | Ouyang ............ A61B 1/00048 |
| 2017/0265879 | A1* | 9/2017 | Washburn, II ......... A61B 1/015 |
| 2019/0246873 | A1 | 8/2019 | Lu |
| 2019/0261845 | A1 | 8/2019 | Jensen |

FOREIGN PATENT DOCUMENTS

| | | |
|---|---|---|
| CN | 2045622718 | 8/2018 |
| CN | 109077698 | 12/2018 |
| CN | 110868905 | 3/2020 |
| KR | 101655653 | 9/2016 |
| WO | 2017192960 | 11/2017 |
| WO | 2019008103 | 1/2019 |

* cited by examiner

ENDOSCOPY DEVICES AND METHODS OF USE

REFERENCE TO RELATED APPLICATION

This patent application claims the benefit of and incorporates by reference U.S. Provisional Patent Application Ser. No. 62/630,718, filed on Feb. 14, 2018. All publications, patents, and patent applications mentioned in this specification are herein incorporated by reference to the same extent as if each individual publication, patent, or patent application was specifically and individually indicated to be incorporated by reference.

FIELD

This patent specification generally relates to a medical device for use in tissue examinations and endoscopic surgery such as in hysteroscopy and urology. More particularly, some embodiments relate to endoscopy system that includes a disposable, single-use cannula and distal imaging module, and a reusable, multiple-use handle and display tower.

BACKGROUND

Direct vision medical procedures such as endoscopic procedures are used to examine certain parts of the body, including internal anatomies. For example, hysteroscopy examines the uterus, a cystoscopy examines the urinary bladder, a gastroscopy examines the esophagus, stomach, and/or small intestine, a bronchoscopy examines the throat, larynx, trachea, and/or lower airways, a sigmoidoscopy examines the rectum, a colonoscopy examines the rectum and/or colon, a colposcopy examines the cervix, vagina and/or vulva, a nasal endoscopy examines the nasal and sinus passages, and the like.

Traditionally endoscopic procedures are performed with expensive equipment. Such equipment may include cystoscopes, hysteroscopes, and various others. Such equipment may also include a display tower, which includes camera control unit and illumination control unit. Existing cystoscopes and hysteroscopes are usually reusable devices with metal cannulae and optical lens inside the metal shafts. Other types of cystoscopes and hysteroscopes may include flexible reusable devise, which a flexible cannula which articulation of the tip is often controlled by a pull wire and a joystick at proximal end. Following each procedure, the equipment may require sterilization which may be high in cost or difficult to operate, yet the sterilization or sanitization may not be effective. More recently, partly disposable endoscopes have become available—see for example U.S. Pat. Nos. 8,460,182 and 9,895,048

An endoscope is an elongated tubular structure which is inserted into body cavities to examine them. A conventional endoscope includes a telescope with an objective lens at its distal end. The telescope includes an image-forwarding system. In rigid endoscopes it is a series of spaced-apart lenses. In flexible endoscopes it is a bundle of tiny optical fibers assembled coherently to forward the image. In digital endoscopes which are normally flexible scopes, the imaging sensor may reside at distal of the flexible cannula. However, when a physician maneuvers a deflectable tip with camera (a digital scope) of a cannula inside the patient, a view horizon may be lost and the physician may lose orientation.

It would therefore be desirable to overcome these challenges and provide a cystoscope and/or hysteroscope with disposable cannula portion at low cost. It would be desirable if such a device or system also capture images with a controllable horizontal view at reduced cost. At least some of these objectives will be satisfied by the devices described herein.

SUMMARY

According to some embodiments an endoscopic systems are described that include: a computer processing system; a high-definition display having a display area of at least 12 inches diagonally in electrical communication with the computer processing system for receiving and displaying endoscopic images and a handheld portion. The handheld portion includes: a multiple-use handle portion having mechanical and electrical couplers for accepting a single-use portion and a cable in electrical communication between the multiple-use handle portion and the computer processing system; and a single-use portion that includes an elongated cannula having a camera module mounted on a distal end and having mechanical and electrical couplers on a proximal end configured to releasably couple with the couplers of the multiple-use handle portion when the handle portion and the single-use portion are assembled into the handheld portion. The cannula and camera module are configured to rotate around the central longitudinal axis of the cannula relative to the multiple-use handle portion. The handheld portion also includes: a first sensor configured to detect rotational movement or rotational position of the cannula and camera module about the central axis relative to the multiple-use portion; and a second sensor configured to detect rotational movement or rotational position of the multiple-use handle portion about an axis parallel to the central axis relative to the display monitor.

According to some embodiments, a third sensor can be included which is configured to detect a position of a selected portion of the handheld portion relative to a selected reference frame. The third sensor can include one or more sensors configured to detect a position, in two or more dimensions, of the selected portion of the handheld portion relative to one or more of the processing system, the display, and a patient cavity in which the cannula is inserted. The endoscope system can further include a horizontal view maintaining circuit coupled with at least one of the first and second sensors and the computer processing system and configured to maintain an image provided by the camera module and displayed at the display in a selected orientation relative to the display despite rotation of the single-use portion and/or the multiple-use handle portion. According to some embodiments, the computer processing system can be user-configured to selectively turn off the horizontal view maintaining circuit to thereby allow the orientation of the image on the display to change with rotation of at least one the multiply-use handle portion and the single-use portion.

According to some embodiments, a set of at least two single-use portions can be provided including one that has a working channel for medical instruments to pass therethrough and is configured for therapeutic use and another that lacks a working channel and is configured for diagnostic use. According to some embodiments, the cannula can include an insert that is bendable by hand and retains a selected bent shape to thereby maintain the cannula in a matching bent shape during a medical procedure.

According to some embodiments a surgical drape can be secured to the single-use portion and a sterile package containing the drape in furled shape and also containing the single-use portion. The surgical drape can be configured to unfurl upon opening and form a surgical barrier between the handle portion and a patient while the cannula is used in a patient procedure and to furl around and contain the single-use portion after completion of the procedure.

According to some embodiments, an endoscope includes a set of a multiple-use handle portion and two or more single-use portions. One of the single-use portion one includes a working channel for the passage of medical instruments therethrough while the other has no working channel. The multiple-use handle portion includes mechanical and electrical connectors and each of the single-use portions includes a proximal housing and a cannula extending distally from the housing. Each cannula has a lighting and imaging modules at its distal end. The housing of each of the single-use portions has mechanical and electrical connectors configured to mate with the mechanical and electrical connectors of the multiple-use handle portion for assembly of the multiple-use portion and a selected one of the single-use portions into an assembled endoscope. The cannula of each of the single-use portions is mounted for motion relative to the multiple-use handle portion. A manual controller is included in the multiple-use handle portion. A motion transfer device is provided that couples the manual controller and the cannula of the selected single-use portion to move the cannula in response to manipulation of the manual controller. A sensor is included that responds to motion of the cannula of the selected single-use portion relative to the multiple-use handle portion. The sensor is configured to provide an indication of the motion, which can be, for example, rotation of the cannula about its longitudinal axis relative to the multiple-use handle portion.

According to some embodiments, a method is described that includes providing a set of a multiple-use handle portion and two or more single-use portions one of which has a cannula with a working channel for the passage of medical instruments therethrough while another has a cannula with no working channel. Each of the single-use portions are in a respective sterile package. The method further includes: selecting one of the single-use portions, removing the selected single-use portion from the sterile package thereof, and releasably connecting the selected single-use portion to the multiple-use handle portion by mating with each other mechanical and electrical connectors of each to form an assembled endoscope; inserting the cannula of the assembled endoscope into a body cavity and imaging the cavity with an imaging module at a distal tip of the inserted cannula; selectively rotating the inserted cannula relative to the body cavity by manual operation of a controller on the multiple-use handle portion; sensing rotation of the cannula of the assembled endoscope with a sensor in the multiple-use handle portion; and displaying images provided by the imaging module at a display that is remote from the multiple-use handle portion; and further displaying an indication of the rotation.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
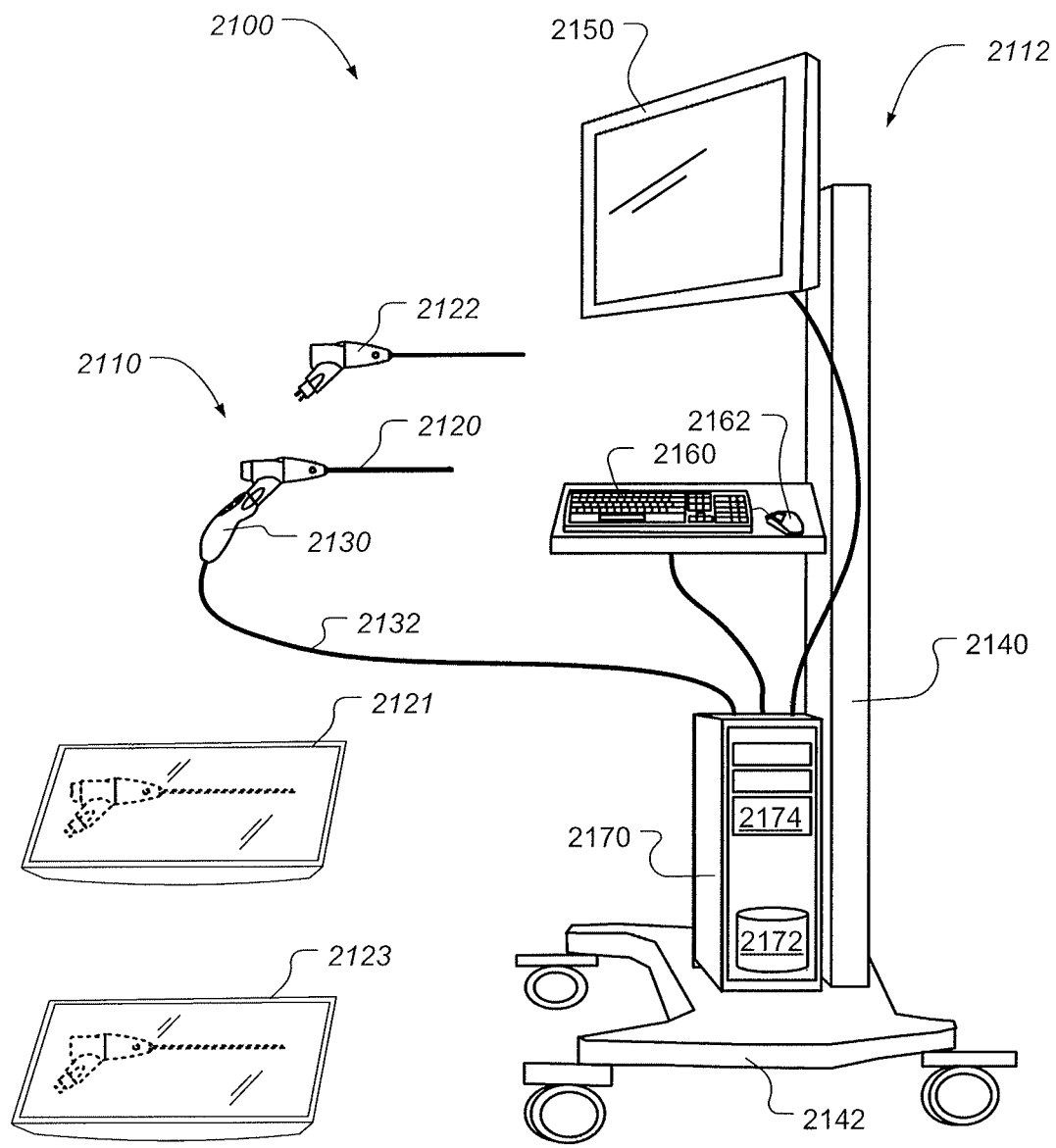
FIG. 1 shows an example of a endoscopy system, according to some embodiments.

A detailed description of examples of preferred embodiments is provided below. While several embodiments are described, it should be understood that the new subject matter described in this patent specification is not limited to any one embodiment or combination of embodiments described herein, but instead encompasses numerous alternatives, modifications, and equivalents. In addition, while numerous specific details are set forth in the following description in order to provide a thorough understanding, some embodiments can be practiced without some or all of these details. Moreover, for the purpose of clarity, certain technical material that is known in the related art has not been described in detail in order to avoid unnecessarily obscuring the new subject matter described herein. It should be clear that individual features of one or several of the specific embodiments described herein can be used in combination with features of other described embodiments or with other features. Further, like reference numbers and designations in the various drawings indicate like elements.

While some exemplary embodiments are directed at cystoscopes and/or hysteroscopes, one of skill in the art will appreciate that this is not intended to be limiting, and the devices described herein may be used for other therapeutic or diagnostic procedures and in other anatomical regions of a patient's body.

The embodiments disclosed herein can be combined in one or more of many ways to provide improved diagnosis and therapy to a patient. The disclosed embodiments can be combined with prior methods and apparatus to provide improved treatment, such as combination with known methods of urological, or gynecological diagnosis, surgery and surgery of other tissues and organs, for example. It is to be understood that any one or more of the structures and steps as described herein can be combined with any one or more additional structures and steps of the methods and apparatus as described herein, the drawings and supporting text provide descriptions in accordance with embodiments.

Although the treatment planning and definition of treatment profiles and volumes as described herein are presented in the context of urological, or gynecological diagnosis or surgery, the methods and apparatus as described herein can be used to treat any tissue of the body and any organ and vessel of the body such as brain, heart, lungs, intestines, eyes, skin, kidney, liver, pancreas, stomach, uterus, ovaries, testicles, bladder, ear, nose, mouth, soft tissues such as bone marrow, adipose tissue, muscle, glandular and mucosal tissue, spinal and nerve tissue, cartilage, hard biological tissues such as teeth, bone and the like, as well as body lumens and passages such as the sinuses, ureter, colon, esophagus, lung passages, blood vessels and throat.

As used herein a processor encompasses one or more processors, for example a single processor, or a plurality of processors of a distributed processing system for example. A controller or processor as described herein generally comprises a tangible medium to store instructions to implement steps of a process, and the processor may comprise one or more of a central processing unit, programmable array logic, gate array logic, or a field programmable gate array, for example.

As used herein, the terms distal and proximal refer to locations referenced from the apparatus, and can be opposite of anatomical references. For example a distal location of a probe may correspond to a proximal location of an elongate member of the patient, and a proximal location of the probe may correspond to a distal location of the elongate member of the patient.

According to various embodiments, a device includes a probing portion for direct insertion into a body cavity. The probing portion is brought into proximity to the tissue and/or area that is to be examined. As used herein, a probe encompasses an object inserted into a subject such as a patient.

FIG. 1 shows an example of a endoscopy system, according to some embodiments. The system 2100 includes a handheld portion 2110 and tower system 2112 which are interconnected via a cable 2132. The handheld portion 2110 includes a single-use disposable portion 2120 and handle portion 2130. The single-use portion 2120 is detachable from handle portion 2130 such that the handle portion 2130 is configured to be used many times. According to some embodiments, different types of versions of the single-use portions can be made available. In the example shown the single-use portion 2120 is configured for therapeutic use and includes a working channel (not shown) through which various devices such as surgical devices can pass through. Also shown in FIG. 1 is a diagnostic single-use portion 2122 that is configured primarily for diagnostic, rather than therapeutic purposes, and does not have a working channel. In some embodiments, several different single-use portions may be supplied as a set of, for example, a single-use portion configured for therapeutic purposes and a single-use portion configured for diagnostic purposes, or a set of single-use portions that have different lengths and/or cannula diameters or arrangements of internal lumina. As will be described in further detail, infra, both the therapeutic single-use portion 2120 and diagnostic single-use portion 2122 include a camera module and LED illumination modules on their distal tips as well as one or more internal lumens for carrying fluid. The tower system 2112 includes column 2140 mounted to a wheeled base 2142. The tower system 2112 also includes a display 2150, keyboard and mouse 2160 and 2162 and processing system 2170. According to some embodiments display monitor 2150 can be touch sensitive for receiving user input as well as high resolution. According to some embodiments display 2150 is configured to display high definition graphics at pixel resolutions of 1280×720, 1920×1080, 2048×1080, 2560×1440, 3840×2160, or higher. According to some embodiments, processing system 2170 can be a suitable personal computer or a workstation that includes one or more processing units 2174, input/output devices such as CD and/or DVD drives, internal storage 2172 such as RAM, PROM, EPROM, and magnetic type storage media such as one or more hard disks for storing the medical images and related databases and other information, as well as graphics processors suitable to power the graphics being displayed on display 2150. According to some embodiments, tower system 2112 is powered by a medical grade power supply (not shown). Also shown in FIG. 1 are sterile package or pouch 2121 containing a single-use portion 2120 configured for therapeutic purposes and sterile package or pouch 2123 the containing a single-use portion 2122 configured for diagnostic purposes.

Figure 2A:
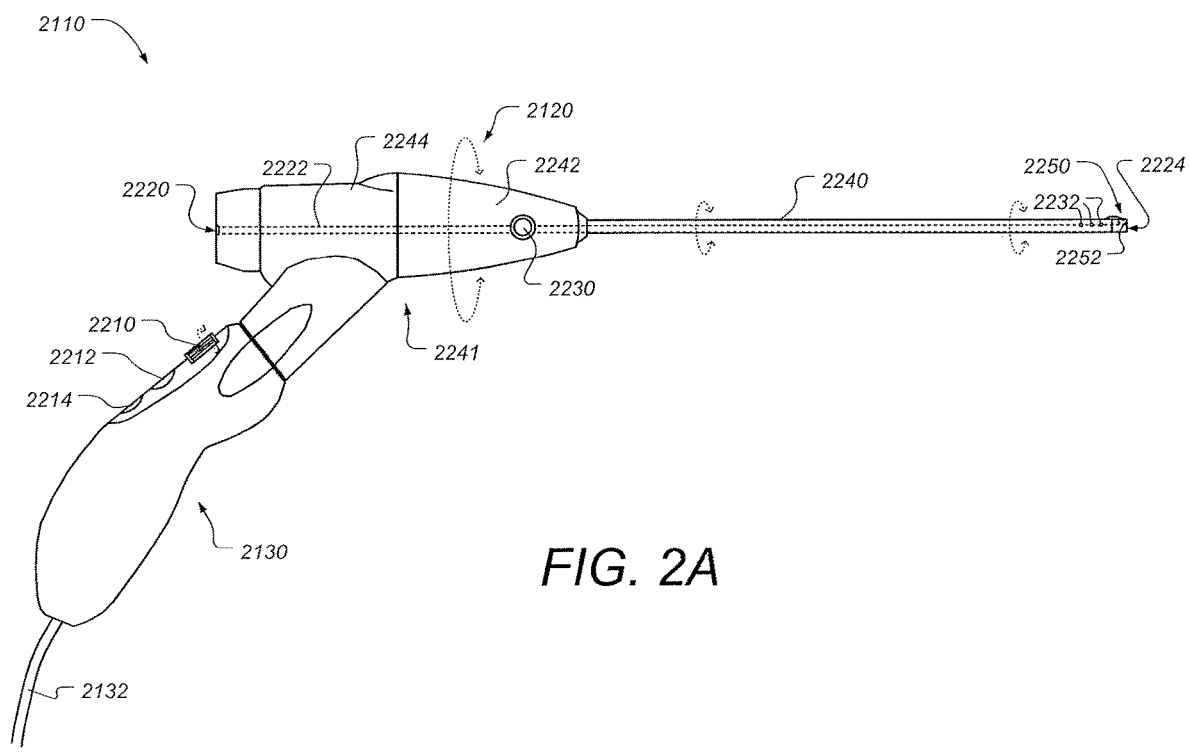
FIGS. 2A and 2B show side views of a hand-held portion of an endoscopy system, according to some embodiments.
Figure 2B:
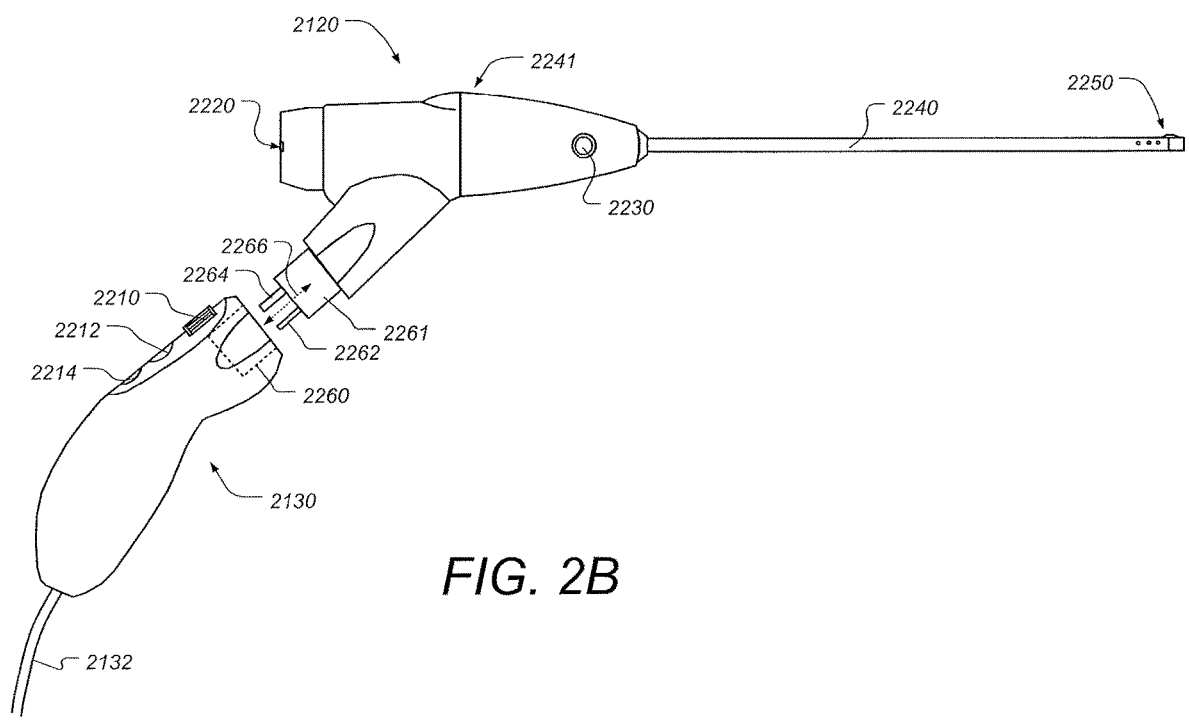

FIGS. 2A and 2B show side views of a hand-held portion of an endoscopy system, according to some embodiments. Hand-held portion 2110 generally includes a reusable handle portion 2130 and a single-use portion 2120. According to some embodiments, single-use portion 2120 may be delivered to the medical practitioner in pre-sterilized package and is intended to be disposed of after a single-use, while the handle portion 2130 is designed to be re-used many times. As mentioned, supra, the single-use portion 2120 in this example is a therapeutic single-use portion that includes a working channel. The therapeutic single-use portion 2120 includes an elongated cannula 2240 having a distal tip 2250. Distal tip 2250 includes a camera module 2252, working channel distal port 2224, and fluid ports 2232. Working channel 2222 is shown in dotted outline and extends from a proximal port 2220 through to the distal port 2224. According to some embodiments, the working channel has an inner diameter of about 3.2 mm such that man standard surgical devices can be disposed therein to carry out various surgical procedures. Examples of such devices include: injection needles, forceps, tubes, knives, snares, probes, coagulator devices, brushes, laser devices, microwave devices (e.g. for ablation), and photodynamic tools.

The cannula 2240 may be long, thin, and semi-rigid. According to some embodiments, the cross-section of cannula 2240 perpendicular to its main longitudinal axis may be substantially circular. It should be noted the cross-section may have any suitable shape such as oval shaped. The diameter of the cannula may differ depending on the sort of endoscopy, such as from 1 mm and up to 15 mm. Besides the working channel, cannula 2240 may have internal structures to support various functionalities. For example, the cannula may comprise one or more fluid channels in fluid communication with various fluid ports. The cannula may comprise one channel to be shared by an inflow and an outflow. Alternatively, the cannula may comprise two or more channels with separate inflow and outflow. According to some embodiments, cannula 2240 also includes a fluid lumen that is fluidically isolated from the working channel. The fluid lumen can be in fluid communication with the distal fluid ports 2232 as well as a proximal fluid port such as fluid port 2230. According to some embodiments another proximal fluid port is provided on the opposite side from port 2230. Cannula 2240 is also configured to accommodate a plurality of electrical conductors used to provide power, control signals to and receive video and image data from to the camera module and lighting modules at distal tip 2250. In some cases the conductors can be insulated and disposed within a separate lumen within cannula 2240, in other cases some or all of the conductors can be disposed within a lumen that is also used for another purpose (e.g. fluid and/or device/tool channel). According to some embodiments one or more optical fibers can pass through cannula 2240 for purposes of data transmission and/or supplying illumination light to distal tip 2250.

Handle portion 2130 is configured to be used many times and is adapted to repeated receive the single-use portions. Handle portion 2130 includes a main body that is dimensioned and shaped to allow secure and ergonomic grasping by the operator's hand. Handle portion 2130 also includes several buttons such as button 2212 and 2214 that can be configured to allow execution of common tasks during use. For example, the buttons 2212 and 2214 can be programmed to control LED lighting level (of LEDs, not shown, at the distal tip 2250), capture still images and/or start and stop recording to video images.

According to some embodiments, cannula 2240 is rotatable about its longitudinal axis relative to the handle portion 2130. In such cases handle 2130 can also include a cylindrical dial 2210 that is configured to rotate lumen 2240 (and distal tip 2250) as shown with the dotted arrows. According to some embodiments, the distal portion 2242 of a housing 2241 that surrounds a proximal portion of the cannula 2240 rotates with the cannula 2240 while the proximal portion 2244 of the housing 2241 remains fixed relative to the handle portion 2130. FIG. 2B illustrates how the single-use portion 2120 can be mounted and removed from multiple-use handle portion 2130. In particular, handle portion 2130 includes a socket 2260 that is dimensioned to couple with male mating portion 2261 that protrudes from single-use portion 2120. The action of mounting and un-mounting is shown by dotted arrow 2266. Protruding from mating portion 2261 is an electrical connector 2262 and cannula 2264 that is used to provide rotation of cannula 2240 when dial 2210 is actuated. According to some embodiments cannula 2264 has a "D" shape cross section or other shape that provides secure rotational coupling between cannula 2264 and a female socket (not shown) in handle 2130.

According to some embodiments, the handle portion 2130 may house or comprise components configured to processing image data, generate control signals, provide power, or establish communication with other external devices. In some cases, the communication may be wireless or wired communication. For example, the wireless communications may include Wi-Fi, radio communications, Bluetooth, IR communications, or other types of direct communications. In some embodiments, the handle portion may be housing sensor assembly to measure a relative position between the cannula and the handle portion. In other embodiments, the sensor assembly may measure relative position or orientation of the handle to its environment. Examples of such sensor assemblies are described further below. In some cases, the handle portion may have a display device configured to provide a user input device or have any type user interactive component, such as a button, mouse, joystick, trackball, touchpad, pen, image capturing device, motion capture device, microphone, or touchscreen.

Figure 3:
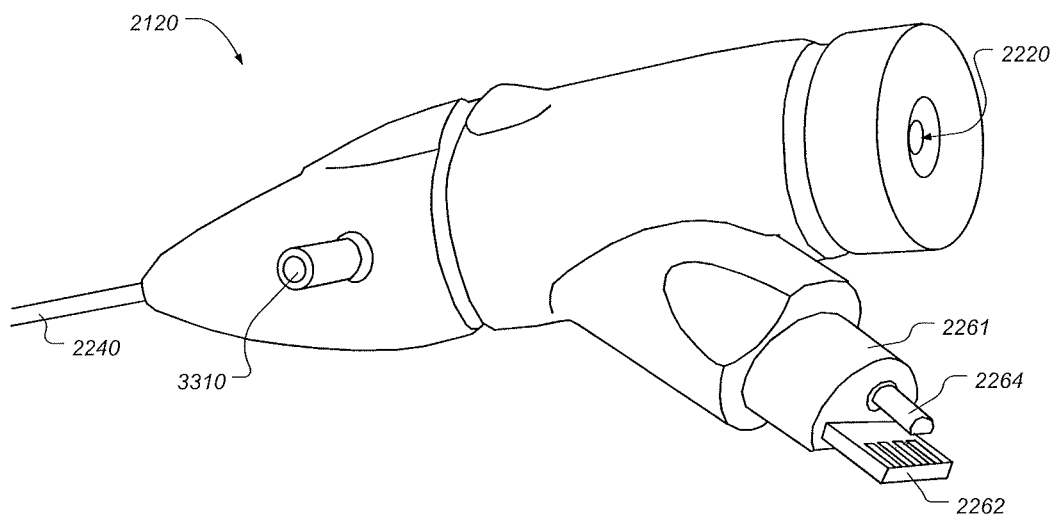
FIG. 3 is a perspective view of the a single-use portion of an endoscopy system with horizontal view management, according to some embodiments.

FIG. 3 is a perspective view of the a single-use portion of an endoscopy system with horizontal view management, according to some embodiments. In this proximal prospective view, the "D" cross-section shape of shaft 2264 and detail of the electrical connector 2262 are shown. Also visible is the left side proximal fluid port 3310 and the proximal working channel port 2220.

Figure 4A:
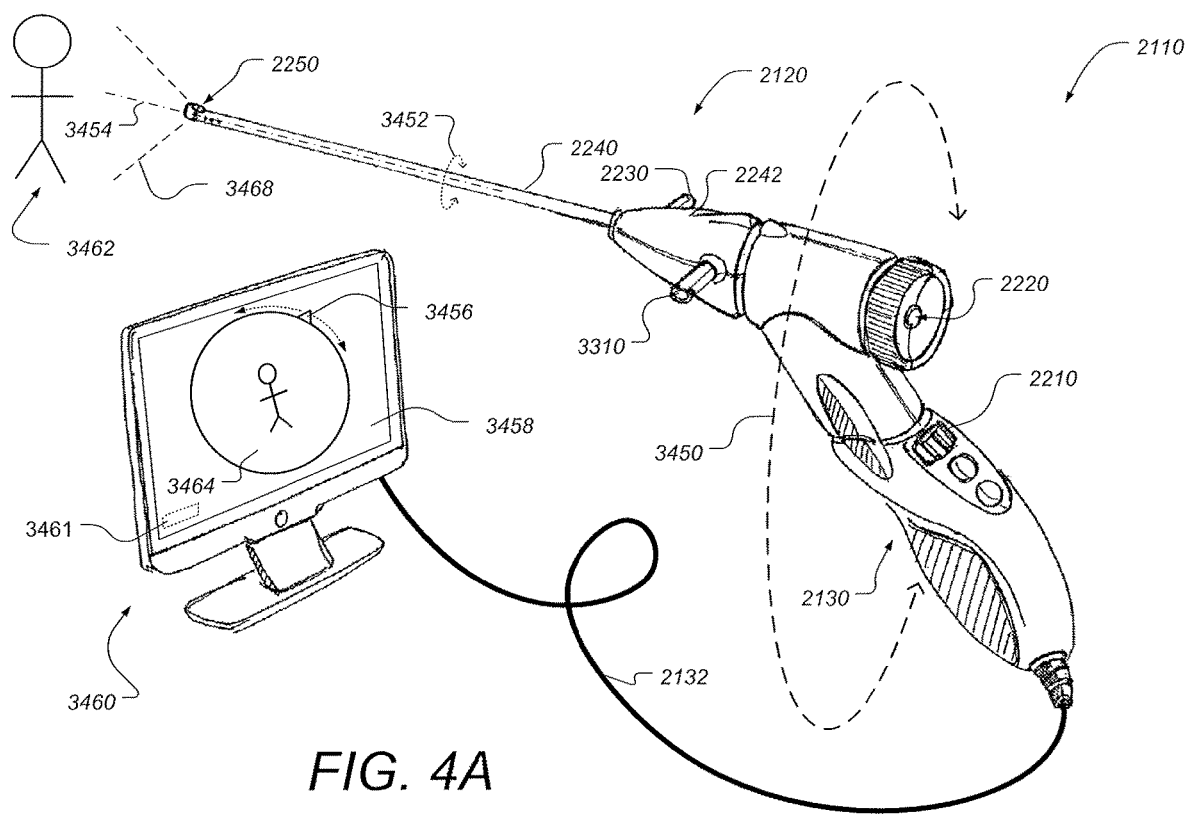
FIG. 4A is a diagram illustrating aspects an endoscopy system with horizontal view management, according to some embodiments.

FIG. 4A is a diagram illustrating aspects an endoscopy system with horizontal view management, according to some embodiments. A simplified endoscopy system is shown that is functionally similar to system 2100 shown in FIG. 1. Handheld portion 2110 is shown connected to an integrated computer system 3460. Note that computer system 3460 can include the similar or identical functionality as the tower system 2112. System 3460 includes a display monitor 3458 that is similar or identical to display 2150 shown in FIG. 1. According to some embodiments, horizontal view management is provided that allows the operator view appropriately oriented images on an external display 3458 (and display 2150 on tower system 2112 shown in FIG. 1) despite relative rotation of the camera module 2252 mounted at distal tip 2250. Note that the camera at the distal tip can be rotated relative to the display monitor in at least two distinct ways. First, the cannula can be rotated relative to the handle portion, depicted with dotted arrow 3452. Second, the entire hand-held portion 2110 can be rotated relative to the display monitor, depicted with dashed arrow 3450. If either or both of these rotations occur, then the uncorrected image displayed on the display monitor may not be correctly oriented. A horizontal plane of the image may be maintained relative to the environment (e.g., gravity, patient anatomy, bed, etc). This is illustrated in FIG. 4A with subject 3462 being captured by the camera module having a direction of view 3468 and displayed as a circular image 3464 on display monitor 3458. According to some embodiments, the "roll" angle (rotation about cannula axis 3454) of the camera module in tip 2250 may be measured with aid of multiple sensors such that the image data may be automatically adjusted to maintain a horizontal view. Alternatively, the horizontal view of the image data may be maintained or corrected with algorithmic method (e.g., optical flow) without using of sensors. According to some embodiments, a roll angle indicator 3456 is displayed on the outer periphery of image circle 3464 to indicate the relative angular position of the camera module about axis 3454. Also shown within handle portion 2130 is electrical connector 3412 that is configured to electrically couple with electrical connector 2262 on single-use portion 2120 (see FIG. 4B).

Figure 4B:
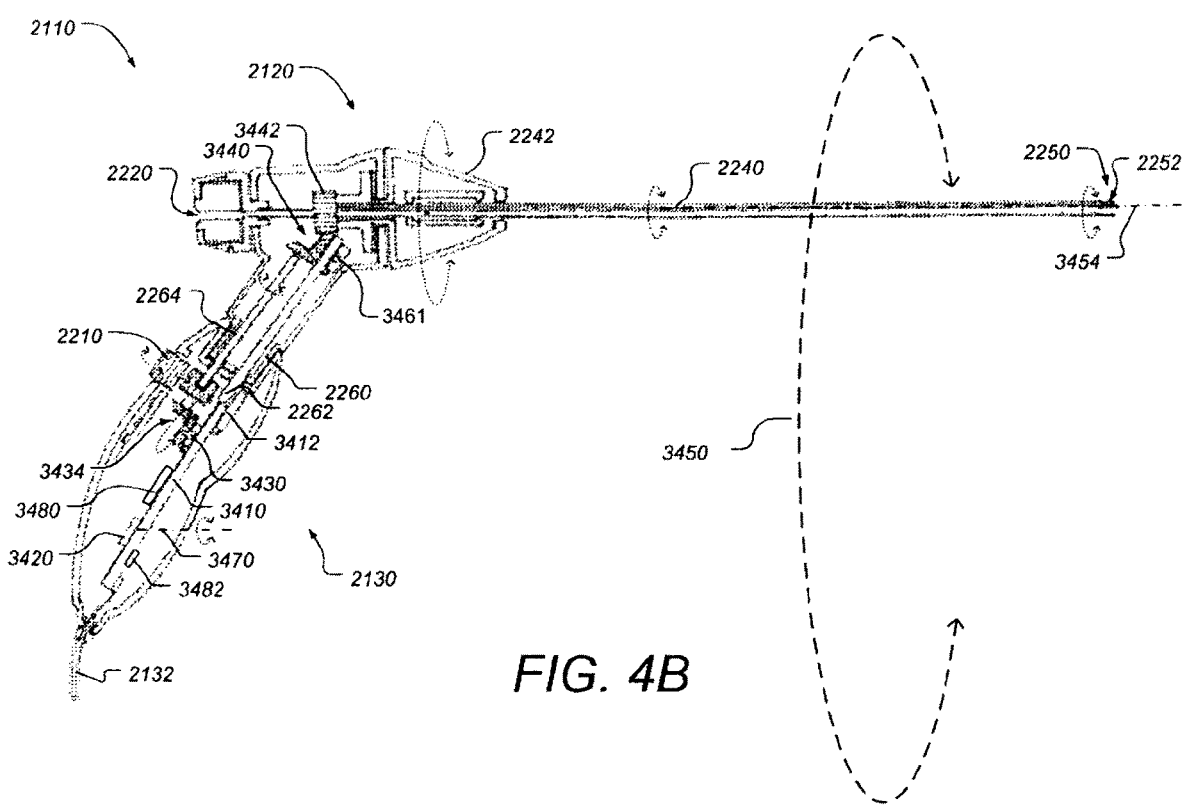
FIG. 4B is a cross sectional view of a hand-held portion of an endoscopy system having horizontal orientation sensors, according to some embodiments.

FIG. 4B is a cross sectional view of a hand-held portion of an endoscopy system having horizontal orientation sensors, according to some embodiments. In this example, the dial 2210 is actuated by the user to rotate the cannula 2240 around its axis 3454. Dial 2210 is meshed with a set of gears 3434 within handle portion 2130 such that when dial 2210 is rotated, it rotates both shaft 2264 and gear 3434. Gear 3434 is attached to rotational sensor 3430 that is mounted on printed circuit board 3410. Sensor 3430 may be an angular position or angular rotational sensor. According to some embodiments, sensor 3430 can be an encoder, potentiometer, and/or hall sensor. Shaft 2264 rotates gear 3442 though gears 3440. Gear 3442 is fixed to rotating portion 2242 of the housing and cannula 2240 and therefore gear 3442, portion 2242, cannula 2240 and camera module 2252 all rotate together around axis 3454. Thus the rotational sensor 3430 measures the rotational position of the cannula and camera module relative to the handle portion. According to some embodiments, the rotational position of the cannula and camera module relative to the handle portion a rotational can be measured by a sensor 3461 which is located within the single-use portion 2120 (or 2122 in the case of FIG. 10).

According to some embodiments, the one or more sensors for measuring an attitude or orientation of the imaging device or optical elements of the imaging device may include an integrated inertial measurement unit (IMU) 3420 mounted on printed circuit board 3410. In general, the inertial measurement sensors may comprise one or more gyroscopes, velocity sensors, accelerometers, magnetometers, or one or more location sensors. The inertial sensors may be used for obtaining data indicative of a spatial disposition (e.g., position, orientation, or angle) and/or motion characteristic (e.g., translational (linear) velocity, angular velocity, translational (linear) acceleration, angular acceleration) of the imaging device. An inertial sensor may be used herein to refer to a motion sensor (e.g., a velocity sensor, an acceleration sensor such as an accelerometer), an orientation sensor (e.g., a gyroscope, inclinometer), or an IMU having one or more integrated motion sensors and/or one or more integrated orientation sensors (such as IMU 3420). According to some embodiments, IMU 3420 is configured to provide sensing data relative to a single axis of motion 3470 that is parallel to cannula axis 3454. According to some other embodiments, a plurality of inertial sensors can be used, with each inertial sensor providing measurements along a different axis of motion. An accelerometer is able to measure an orientation of the sensor in an earth gravitational field. The orientation angle with respect to the earth/world gravitational field can be obtained by a rotation matrix from the ground reference frame to the accelerometer sensor body frame. The accelerometer can be a single-axis accelerometer or three-axis accelerometer. Three angular accelerometers can be used to provide angular acceleration data along three different axes of motion. The three directions of motion may be orthogonal axes. One or more of the angular accelerometers may be configured to measure acceleration around a rotational axis. As another example, three gyroscopes can be used to provide orientation data about three different axes of rotation. Alternatively, at least some or all of the inertial sensors may provide measurement relative to the same axes of motion. Such redundancy may be implemented, for instance, to improve measurement accuracy. A single inertial sensor may be capable of providing sensing data relative to a plurality of axes. For example, IMU 3420 can include a plurality of accelerometers and gyroscopes that can be used to generate acceleration data and orientation data with respect to up to six axes of motion. In some cases, the attitude data about the imaging device may include rotational angle of the imaging device with respect to up to three rotational axes. A variety of methods can be used to derive attitude data of the imaging device such as Kalman filter, Extended Kalman filter complimentary filter and various other sensor fusion algorithms. According to some other embodiments, one or more sensors may be located on the cannula or in other locations than depicted in FIG. 4B. For example, one or more sensors may be enclosed in the distal tip 2250.

The orientation or "roll" rotational position measured by sensors 3430 and 3420 is used to process the imaging data in order to maintain a horizontal view. The image data may be processed by one or more processors in handle portion 2130 and/or in processing 2170 (shown in FIG. 1) or computer system 3460 (shown in FIG. 4A). In some embodiments, one or more processors (e.g. processors(s) 2174 in FIG. 1 and/or processor(s) 3461 in FIG. 4A) may be configured to calculate the attitude data of the imaging device and transform the image data based on the attitude data. In some embodiments, the one or more processors may be a programmable processor (e.g., a central processing unit (CPU) or a microcontroller), a field programmable gate array (FPGA) and/or one or more Advanced RISC Machine (ARM) processors. In some embodiments, the one or more processors may be operatively coupled to a non-transitory computer readable medium. The non-transitory computer readable medium can store logic, code, and/or program instructions executable by the one or more processors for performing one or more steps. The non-transitory computer readable medium can include one or more memory units (e.g., removable media or external storage such as an SD card or random access memory (RAM)). In some embodiments, some or all of the orientation correction image processing can be carried out within the multi-use handle portion 2130. For example in FIG. 4B the calculations and other image transformation processing can be carried out on a general processor unit 3480 and/or image signal processor 3482, which are both mounted on circuit board 3410.

According to some other embodiments, the horizontal view may be maintained without using sensors. For example, optical methods such as optical flow may be used to track motion vectors between consecutive image frames such that a global rotation of the view may be tracked. The video data may then be processed to maintain a horizontal view.

In some cases, the view with maintained/corrected horizon is displayed on a monitor 2150 in FIG. 1 or monitor 3458 in FIG. 4A. According to some embodiments, multiple horizon view control options are provided for a user to select. For example, the view with maintained/corrected horizon can be turned on or off by software configurations to allow users to adjust based on their needs. In another example, a user may select from multiple horizon view control options including: fully automated horizon control relative to ground reference, horizon control relative to handle portion, manual control, horizon control relative to a user selected reference and various others. In some examples one of the buttons (e.g. button 2212 or button 2214 shown in FIG. 2A) can be programmed to allow the user to change the horizontal view configuration.

Figure 5:
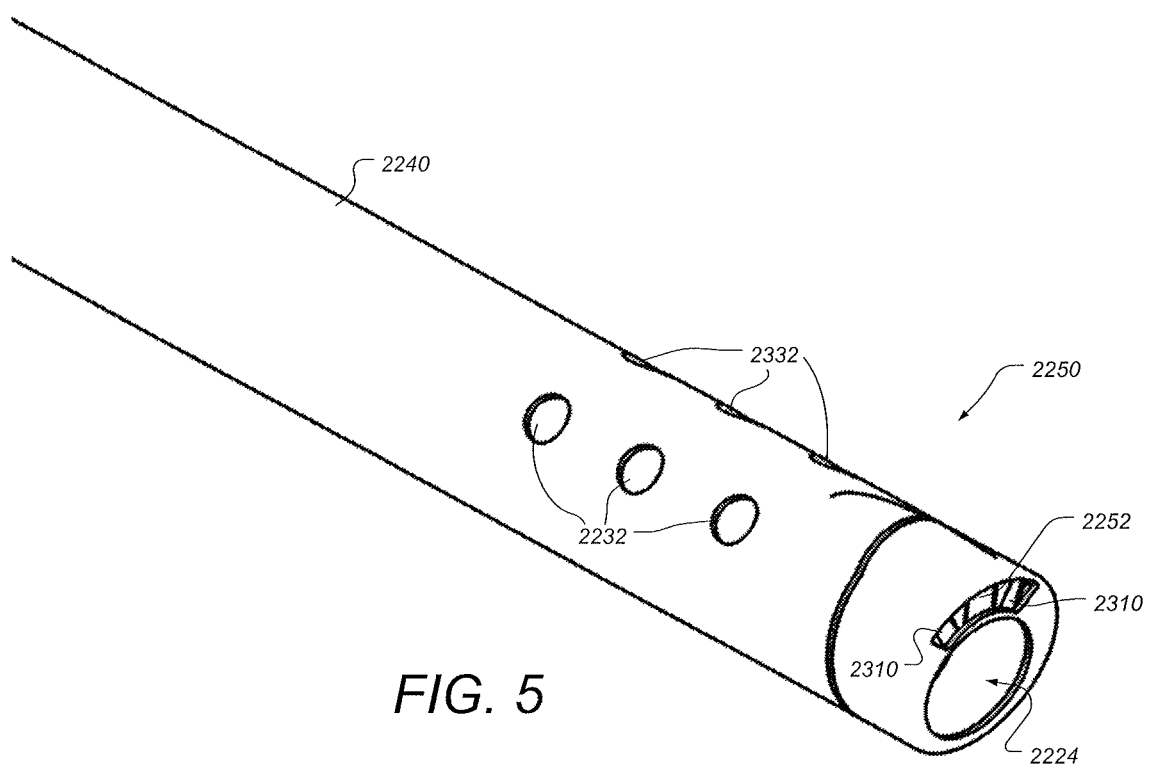
FIG. 5 is a perspective view showing further detail of the distal tip of a hand-held portion of an endoscopy system configured for therapeutic use, according to some embodiments.

FIG. 5 is a perspective view showing further detail of the distal tip of a hand-held portion of an endoscopy system configured for therapeutic use, according to some embodiments. Visible is the distal end of cannula 2240 and distal tip 2250. The distal tip 2250 includes camera module 2252 and LED light sources 2310. Also shown are the fluid ports 2232 and 2332 and the distal working channel port 2224. According to some embodiments, the working channel port 2224 is also configured for in-flow (flowing fluid out of the device and into the patient) and fluid ports 2232 and 2332 are configured for out-flow (into the device and out of the patient).

Figure 6:
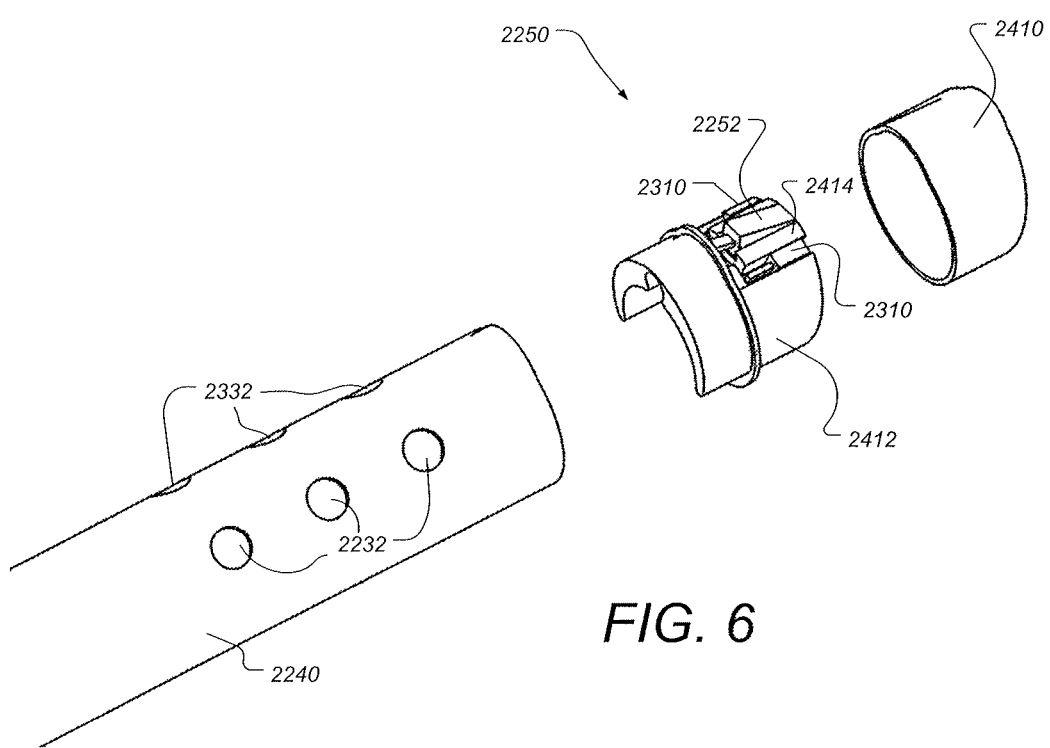
FIG. 6 is a perspective view showing further detail of the distal tip of a hand-held portion of an endoscopy system configured for therapeutic use, according to some embodiments.

FIG. 6 is a perspective view showing further detail of the distal tip of a hand-held portion of an endoscopy system configured for therapeutic use, according to some embodiments. Visible in this exploded view is how the distal tip 2250 is attached to the cannula 2240. Distal tip 2250 includes a tip housing 2410 that surrounds the distal portion tip module 2412. The proximal portion of module 2412 is inserted into and bonded to the distal end of cannula 2240. Module 2412 includes a carrier 2414 onto which camera module 2252 and LEDs 2310 are mounted. Note that carrier 2414 is configured in this example to hold camera module in a slightly downward angle of view. That is, the camera module 2252 is pointed downwards such that its view is biased towards the working channel distal port 2224 (shown in FIG. 5)

Figure 7A:
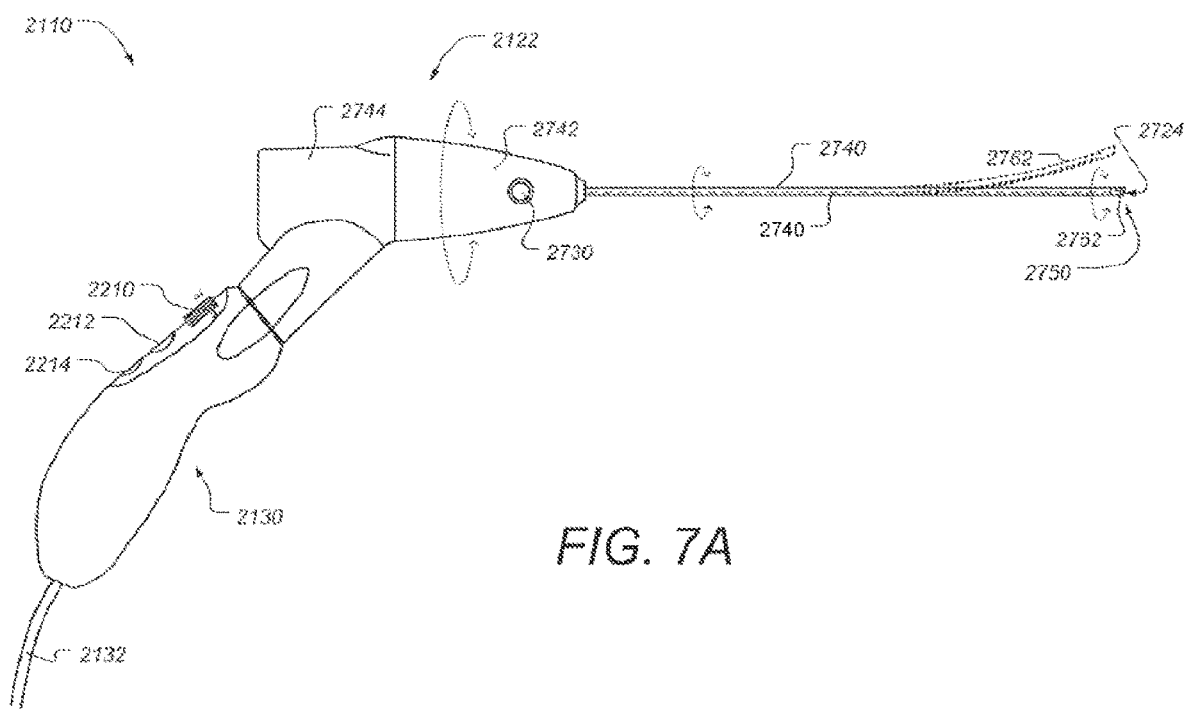
FIGS. 7A and 7B show side views of a hand-held portion of an endoscopy system configured for diagnostic use, according to some embodiments.
Figure 7B:
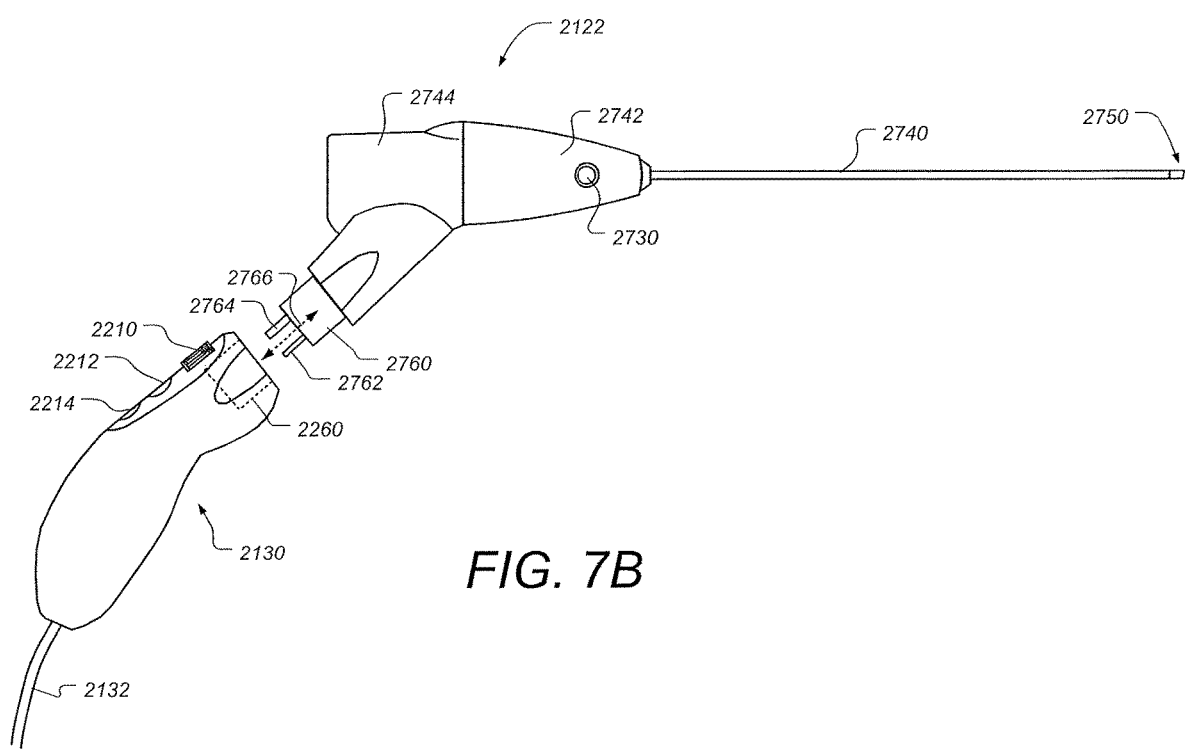

FIGS. 7A and 7B show side views of a hand-held portion of an endoscopy system configured for diagnostic use, according to some embodiments. Hand-held portion 2110 in this case includes a reusable handle portion 2130 and a diagnostic single-use portion 2122. Note that many of the components of single-use potion 2122 are similar or identical to the components of single-use portion 2120 shown in and described with respect to FIGS. 2A, 2B, 3, 4A, 4B, 5 and 6. Many of the embodiments that are shown in those figures and described herein for single-use portion 2120 apply equally to single-use portion 2122 and will not be repeated for purposes of clarity. According to some embodiments, single-use portion 2122 may be delivered to the medical practitioner in pre-sterilized package and is intended to be disposed of after a single-use, while the handle portion 2130 is designed to be re-used many times. As mentioned, supra, the single-use portion 2122 in this example is a diagnostic single-use portion that does not include a working channel. The diagnostic single-use portion 2122 includes an elongated cannula 2740 having a distal tip 2750. Distal tip 2750 includes a camera module 2752, and distal fluid ports 2724.

The cannula 2740 may be long, thin, and semi-rigid. According to some embodiments, the cross-section of cannula 2740 perpendicular to its main longitudinal axis may be substantially circular. It should be noted the cross-section may have any suitable shape such as oval shaped. The diameter of the cannula may differ depending on the sort of endoscopy, such as from 1 mm and up to 15 mm. Cannula 2740 may have internal structures to support various functionalities. For example, the cannula may comprise one or more fluid channels in fluid communication with various fluid ports. The cannula may comprise one channel to be shared by an inflow and an outflow. Alternatively, the cannula may comprise two or more channels with separate inflow and outflow. The fluid lumen can be in fluid communication with the distal fluid ports 2724 as well as a proximal fluid port such as fluid port 2730. Cannula 2740 is also configured to accommodate a plurality of electrical conductors used to provide power, control signals to and receive video and image data from to the camera module and lighting modules at distal tip 2750. In some cases the conductors can be insulated and disposed within a separate lumen within cannula 2740, in other cases some or all of the conductors can be disposed within a lumen that is also used for another purpose (e.g. fluid and/or device/tool channel). According to some embodiments one or more optical fibers can pass through cannula 2740 for purposes of data transmission and/or supplying illumination light to distal tip 2750.

According to some embodiments, cannula 2740 is rotatable about its longitudinal axis relative to the handle portion 2130. In such cases handle 2130 can also include a cylindrical dial 2210 that is configured to rotate lumen 2740 (and distal tip 2750) as shown with the dotted arrows. According to some embodiments, the distal portion 2742 of the housing rotates with the cannula 2740 while the proximal portion 2744 of the housing remains fixed relative to the handle portion 2130. FIG. 7B illustrates how the single-use portion 2122 can be mounted and removed from multiple-use handle portion 2130. In particular, handle portion 2130 includes a socket 2260 that is dimensioned to couple with male mating portion 2760 that protrudes from single-use portion 2120. The action of mounting and un-mounting is shown by dotted arrow 2766. Protruding from mating portion 2760 is an electrical connector 2762 and shaft 2764 that is used to provide rotation of cannula 2740 when dial 2210 is actuated.

Figure 8:
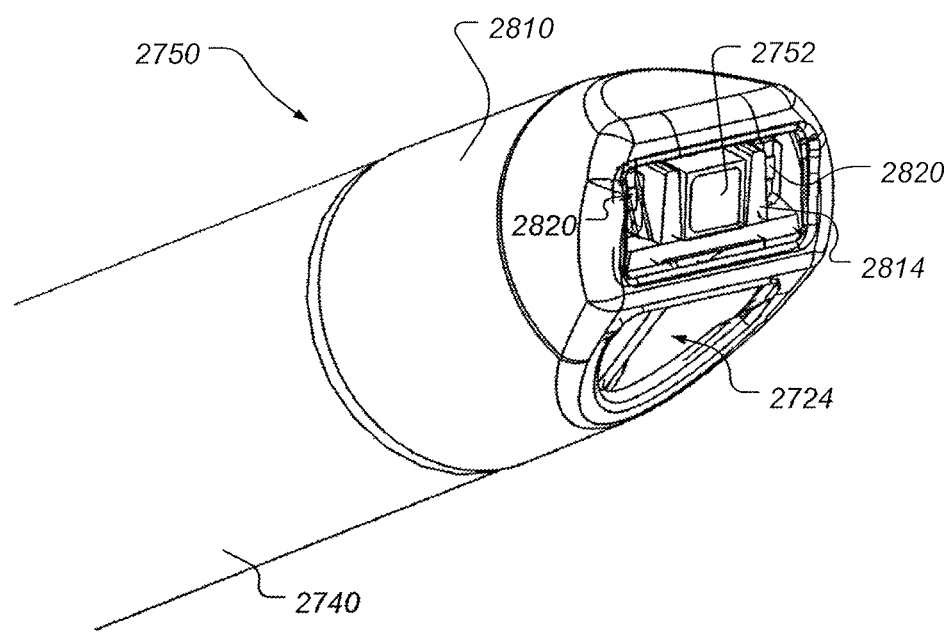
FIG. 8 is a perspective view showing further detail of the distal tip of a hand-held portion of an endoscopy system configured for diagnostic use, according to some embodiments.

FIG. 8 is a perspective view showing further detail of the distal tip of a hand-held portion of an endoscopy system configured for diagnostic use, according to some embodiments. Visible is the distal end of cannula 2740 and distal tip 2750. The distal tip 2750 includes camera module 2752 and LED light sources 2820. Also shown are two fluid ports 2724. According to some embodiments, one fluid port is configured for in-flow (flowing fluid out of the device and into the patient) and is configured for out-flow (into the device and out of the patient). Similarly to distal tip 2250 (e.g. shown in FIG. 6 distal tip 2750 is a separate assembly attached to the cannula 2740. Distal tip 2750 includes a tip housing 2810 that surrounds a distal portion tip module (not shown). The proximal portion of the distal tip module is bonded to the distal end of cannula 2740. A carrier 2814 holds camera module 2752 and LEDs 2820. Note that carrier 2814 is configured in this example to hold camera module in a slightly downward angle of view. That is, the camera module 2752 is pointed downwards such that its view is biased towards the fluid ports 2724.

Figure 9:
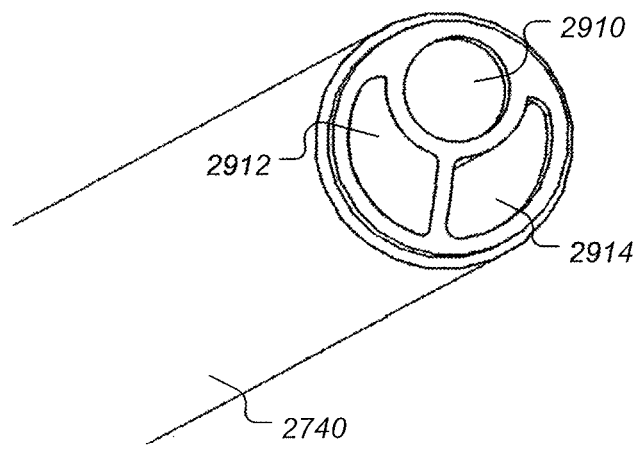
FIG. 9 is a perspective view showing some of the inner structures of a cannula used for diagnostic use, according to some embodiments.

FIG. 9 is a perspective view showing some of the inner structures of a cannula used for diagnostic use, according to some embodiments. In this view, three lumens are visible. Lumen 2910 that is used for carrying the electrical wires that connect the camera module and LEDs with the electrical connector 2762. Lumens 2912 and 2914 are configured for carrying fluid between the proximal fluid ports (e.g. 2730 in FIGS. 7A and 7B) and the distal fluid ports 2724.

Figure 10:
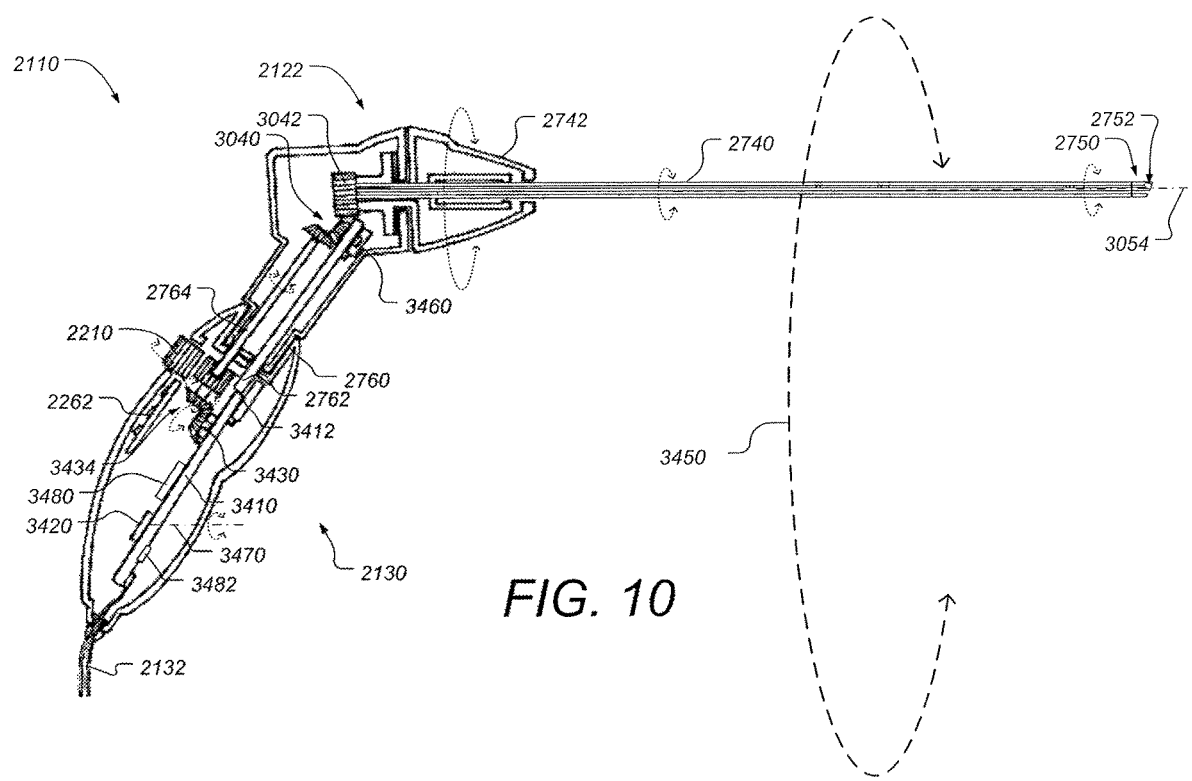
FIG. 10 is a cross sectional view of a hand-held portion of an endoscopy system configured for diagnostic use having horizontal orientation sensors, according to some embodiments.

FIG. 10 is a cross sectional view of a hand-held portion of an endoscopy system configured for diagnostic use having horizontal orientation sensors, according to some embodiments. In this example, the dial 2210 is actuated by the user to rotate the cannula 2740 around its axis 3054. Dial 2210 is meshed with a set of gears 3434 within handle portion 2130 such that when dial 2210 is rotated, it rotates both shaft 2764 and gear 3434. Gear 3434 is attached to rotational sensor 3430 that is mounted on printed circuit board 3410. Shaft 2764 rotates gear 3042 though gears 3040. Gear 3042 is fixed to rotating portion 2742 of the housing and cannula 2740 and therefore gear 3042, portion 2742, cannula 2740 and camera module 2752 all rotate together around axis 3054. The rotational sensor 3430 measures the rotational position of the cannula and camera module relative to the handle portion.

Bendable Cannula.

Cystoscopes, hysteroscopes or devices for direct vision of the inside of the uterus and bladder, have been shown to improve diagnostic accuracy. However, patients often find the insertion and removal of the hysteroscopy apparatus and, subsequently, the presence of an endoscopic apparatus into the patient's uterine cavity uncomfortable. Typical hysteroscopy devices have a distal tip end sized to facilitate insertion of the tip end through the patient's cervix and into the uterus to obtain tissue samples for diagnostic purposes.

According to some embodiments, a bendable cannula is provided. Referring to FIG. 7A, the cannula 2740 may comprise a portion made of flexible material (e.g., plastic) and a bendable insert 2760 made of a material (e.g., metal) that can be bent to reach a desired shape as shown by dotted outline 2762. The cannula may be disposable. Alternatively, the cannula can be sterilized and re-used. The cannula may be deformed or bent at the time of usage to aid reaching recessed portions of the uterine cavity. In the illustrated example, the cannula can be made bendable, for example, by using a flexible material (e.g., plastic, nylon) that includes one or more inserts 2760 which can be bendable metal wires, tubes, flat rods or similar running along the inside length of the cannula housing. The cannula can be made of any suitable material such as Provista Copolymer, vinyl (such as polyvinyl chloride), Nylon (such as vestamid, grillamid), pellethane, polyethylene, polypropylene, polycarbonate, polyester, silicon elastomer, acetate and so forth.

According to some embodiments, the cannula may be deformed or bent at the time of usage to change or adjust the direction of view (DOV) of the distal camera. A conventional cannula may have an optical prism inside rod lenses at certain degrees near the distal end to be suitable for many applications. For example, the optical prism may provide a direction of view (DOV) at various degrees (e.g., 30 degrees, 70 degrees or any number between 0 and 180 degrees) in order to enlarge a field of view. However, when an imaging sensor is situated at the distal tip, such optical prism may cause a very large packaging at distal end or greatly increase the cost of the camera module. In one embodiment, a bendable or deformable cannula can adjust the DOVs by user's manual deformation of the preferred bend of the cannula at various angles such that the optical axis of the imaging device intersects with the longitude axis of the cannula at the imaging device. For instance a bent cannula may be positioned such that the optical axis (i.e., DOV) of the imaging device is oblique to the axis of the cannula at 5 degrees, 10 degrees, 15 degrees, 20 degrees, 25 degrees, 30 degrees, 35 degrees, 40 degrees, 45 degrees, 50 degrees, 55 degrees, 50 degrees, 55 degrees, 60 degrees, 65 degrees, 70 degrees, 75 degree, 90 degrees, 120 degrees, 150 degrees, up to 180 degrees or any number in between.

The configuration or shape of the cannula may be formed via multiple bends. In some cases, the initial bend of the cannula may not be completely satisfactory, the bent angle can be adjusted by forcing the deformed or bent distal portion. The updated deformed or bent shape is maintained because the internal bendable metal insert 2760 can overcome the stiffness of the external flexible cannula material and hence holds the shape. Ease of bending or deformation depends on the relative stiffness of the internal metal stiffener and external flexible cannula material.

Management of Single-Use of the Disposable Cannula.

According to some embodiments, a detection feature is provided to ensure single-use of the cannula or the disposable portion. For example, the detection feature may be configured to detect a used cannula attached to the handle portion. Upon a detection of a re-use of the disposable portion, a user may be notified of the violation or the device may be disabled from further usage. Various methods can be adopted to enable the single-use detection function. For instance, a re-use of the cannula can be detected via mechanical mechanism, electrical mechanism, with aid of sensors and a combination of any of the above. The detection feature may be implemented using mechanical structures. For instance, a mechanical fuse can be located on the proximal end (e.g., proximal interface) of the single-use portion. The fuse may be destroyed once it is plugged into the handle portion and unplugged from handle portion. In another example, the detection feature may be implemented using electrical structure such as an electrical fuse. For instance, an electrical fuse may be provided on the circuit at the proximal end of the single-use portion. Once the single-use portion is plugged into handle portion, the handle electronics detects its presence and burn the fuse. When the same cannula is plugged into handle again, the handle electronics may detect an open fuse. In some cases, a user may be presented a notice indicating a detected re-use of the cannula. In various other embodiments, the detection feature may be implemented using sensors. Sensors such as Dallas chip, EEPROM, RFID, barcode and the like may be utilized to track the usage of the cannula.

In an example, Dallas chip or EEPROM is used, the sensor (Dallas chip or EEPROM) on the cannula is read by the electronics inside handle. Once detected, the handle electronics will program the sensor and tag is as used, which may be through embedded software programming. In another example, a barcode or RFID configured to be read by a reader may be located on the proximal end of the single-use portion and can be read by a reader located on the handle portion. In some cases, once a re-use is detected, the single-use portion may be configured to be disabled from being used after being read a first time by the reader.

The barcode may define elements such as the version, format, position, alignment, and timing of the barcode to enable reading and decoding of the barcode. The remainder of the barcode can encode various types of information in any type of suitable format, such as binary or alphanumeric information. The barcode may be two dimensional such as PDF417, Aztec, MaxiCode, and QR code, etc. The barcode may be one-dimensional barcode such as Interleaved 2/5, Industrial 2/5, Code 39, Code 39 Extended, Codabar, Code 11, Code 128, Code 128 Extended, EAN/UCC 128, UPC-E, UPC-A, EAN-8, EAN-13, Code 93, Code 93 Extended, DataBar Omnidirectional (RSS-14), DataBar Truncated (RSS-14 Truncated), DataBar Limited (RSS Limited), DataBar Stacked, DataBar Expanded, DataBar Expanded Stacked, etc. The barcode can encode various types of information in any type of suitable format, such as binary, alphanumeric, ASCII, etc., and the code can be based on any standards. The barcode may be read by an optical reader, laser scanner or other imaging device.

Integrated Medical Drape.

Figure 11A:
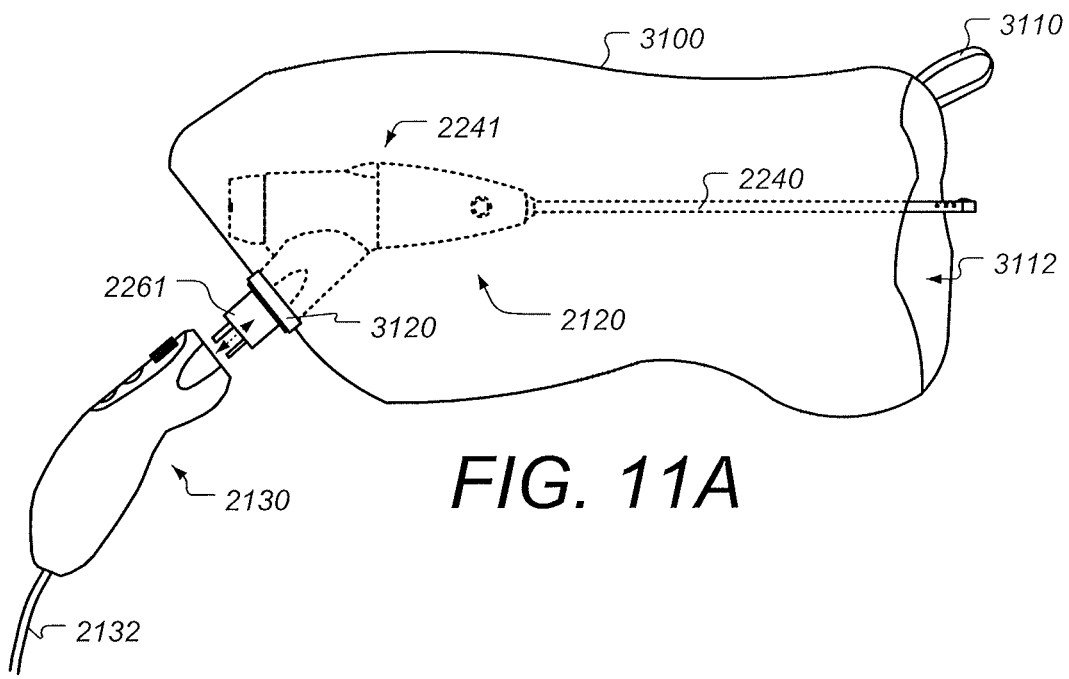
FIGS. 11A and 11B illustrate a medical drape integrated with the single-use portion, according to some embodiments.
Figure 11B:
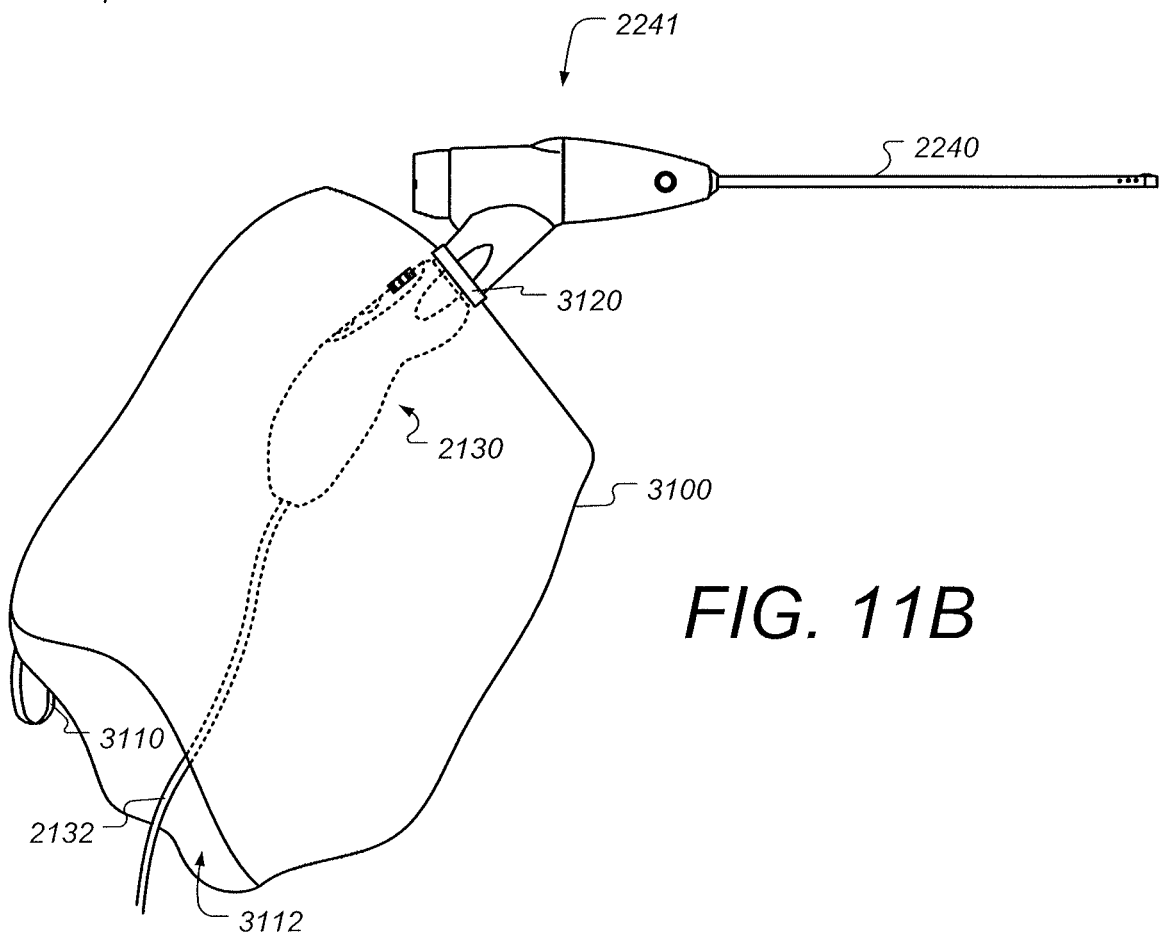

According to some embodiments, a device with an integrated medical drape may be provided. FIGS. 11A and 11B illustrate a medical drape integrated with the single-use portion, according to some embodiments. The medical drape 3100 is shown integrated to the housing of the single use portion 2120 just above the male mating portion 2261. According other embodiments, the drape 3100 can be integrated or attached to single use portion 2120 at other locations such as near the proximal end cannula 2240 or on the distal portion of housing 2241. Although a therapeutic single use portion 2120 is shown in this example, the drape can be similarly integrated with diagnostic single use portions as well. The drape 3100 may be easily deployable to cover the handle portion. During a surgical procedure, the multiple use handle portion 2130 may be covered by the drape such as shown in FIG. 11B. When the procedure is finished, the drape can be easily removed from the handle and folded inside out and can be used as a container to hold the contaminated disposable portion. The drape 3100 may comprise a coupler 3120 configured to couple the drape to the device. The coupler 3120 may be an adaptor ring sized and shaped to be integrated/glued to the proximal portion of the cannula or single-use portion. The coupler 3120 may allow the drape to be assembled to the single-use portion to become an integrated cannula with drape. In some cases, the drape is directly glued, welded or connected to the cannula without an adapter.

The drape may comprise features aiding deploying of the drape before surgical procedures. For example, the drape may comprise a pull loop 3110 that can be used by a physician to pull the drape off the device. The pull loop 3110 may be attached to the main body of the drape via an attachment. Non-sterile persons can access the loop and deploy the drape without contaminating the sterile portion of the drape body. According to some embodiments, loop 3110 is also configured to function as a draw-string to reduce the size of the main opening 3112 of the drape. This can be useful, for example, following use of the single use portion when the drape is turned inside out (i.e. back to the direction shown in FIG. 11A where the draw-string can be used to further close the main opening 3112 to more fully contain the used and contaminated single use portion.

The drape 3100 may be constructed with a sheet of material that is substantially flexible and may be impervious to liquids. The sheet(s) of material may be constructed from readily available plastic films used in the medical field, for example, vinyl (such as polyvinyl chloride), polyethylene, polypropylene, polycarbonate, polyester, silicon elastomer, acetate and so forth.

Authentication of Cannula and Handle.

According to some embodiments, an authentication feature is provided to ensure the single-use cannula is from an authenticated source. For example, the single-use portion may be not be replaced by a non-authenticated cannula from unauthorized other manufacturers. Also, the authentication feature may help to ensure the single-use cannula is not used on a non-authenticated handle from unauthorized other manufacturers. These provisions can provide ensured quality and safety for the above-mentioned medical device. For example, the authentication feature may be configured to detect a cannula or handle with their intrinsic identity (ID). Upon reading the ID from the single-use portion to the handle portion or vice versa, a user may be notified of a violation or the device may be disabled from further usage. Various methods can be adopted to enable the authentication. For instance, a single-use portion or handle portion may be embedded with an EEPROM, RFID, or other secure chip to be detected and read. A single-use portion or handle portion can also have a unique electrical or mechanical signature on single-use portion that is confirmed by handle or system or vice versa. A combination of any of the above may be used to enhance the authentication. In an example, the authentication feature may be implemented using mechanical structures. For instance, mechanical features can be located on the proximal end (e.g., proximal interface) of the single-use portion or distal end of handle portion may be detected and mechanically verified once it is connected. Mechanical features may be special connectors, structure, or special material. In another example, the authentication feature may be implemented using electrical signature from the cannula, handle, or system such as resistance value, impedance value, voltage values or the like. For instance, an electrical circuitry may be provided at the proximal end of the single-use portion or distal portion of handle. Once the single-use portion is plugged into handle portion, the electronic circuitry on cannula, handle and system may detect each other and authenticate each other. When a third-party cannulas or handle is used in the system, the electronics in the rest part of the system may detect a miss match or un-authenticated device. In some cases, a user may be presented a notice indicating a detected un-authenticated cannula or handle. In various other embodiments, the authentication feature may be implemented using sensors. Sensors such as EEPROM, RFID, secure microchip, and the like may be utilized to track the single-use cannula or handle.

In an example, a barcode or RFID configured to be read by a reader may be located on the proximal end of the single-use portion and can be read by a reader located on the handle portion or wise versa. In some cases, once an un-authenticated single-use portion or handle is detected, the un-authenticated portion may be configured to be disabled from the system.

In some embodiments, the Dallas chip, EEPROM, RFID, barcode, mechanical features and the like may also be configured to encode any other information related to the device or the surgery, for example, specification of the cannula, suggested surgery parameters and/or various other information related to the single-use cannula or the surgery using the device.

The barcode may define elements such as the version, format, position, alignment, and timing of the barcode to enable reading and decoding of the barcode. The remainder of the barcode can encode various types of information in any type of suitable format, such as binary or alphanumeric information. The barcode may be two dimensional such as PDF417, Aztec, MaxiCode, and QR code, etc. The barcode may be one-dimensional barcode such as Interleaved 2/5, Industrial 2/5, Code 39, Code 39 Extended, Codabar, Code 11, Code 128, Code 128 Extended, EAN/UCC 128, UPC-E, UPC-A, EAN-8, EAN-13, Code 93, Code 93 Extended, DataBar Omnidirectional (RSS-14), DataBar Truncated (RSS-14 Truncated), DataBar Limited (RSS Limited), DataBar Stacked, DataBar Expanded, DataBar Expanded Stacked, etc. The barcode can encode various types of information in any type of suitable format, such as binary, alphanumeric, ASCII, etc., and the code can be based on any standards. The barcode may be read by an optical reader, laser scanner or other imaging device.

In some embodiments, the device may be in communication with an external computing system such as tower system 2112 in FIG. 1 and/or computer system 3460 in FIG. 4A. The external computing system may be configured to, for example, process image data transmitted from the device to maintain a horizon view, authenticate a cannula using the authentication data transmitted from the device, detect a re-use of a cannula, and various other functions in accordance with various embodiments described herein. The external computing system may optionally be a mobile device, such as a cell phone, smartphone, watch, tablet, remote controller, laptop, or other device. The external computing system may be a stationary device, e.g., personal computer, server computer or other structure. The external computing system may be or comprise a wearable device, such as a helmet, hat, glasses, earpiece, watch, wristband, armband, or any other type of wearable device.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An endoscopic system comprising:
 a computer processing system;
 a high-definition display having a display area of at least 12 inches diagonally in electrical communication with the computer processing system for receiving and displaying endoscopic images; and
 a handheld portion comprising:

a multiple-use portion having mechanical and electrical couplers at a proximal end thereof and a cable in electrical communication between said multiple-use portion and the computer processing system; and a single-use portion that includes a cannula elongated along a cannula axis and having a camera module mounted on a distal end and mechanical and electrical couplers on a proximal end;

wherein said mechanical and electrical couplers of the multiple-use portion are configured to releasably couple with said mechanical and electrical couplers of the single-use portion to thereby form said handheld portion, and wherein the cannula and camera module are configured to rotate around the cannula axis relative to the multiple-use portion;

wherein:

said single-use portion comprises an elongated first proximal part that extends along said cannula axis and a second, elongated and rounded proximal part that extends therefrom along a handle direction that is transverse to said cannula axis;

said multiple-use portion is elongated and rounded and has a proximal end that mates with a distal end of said second, elongated and rounded proximal part of the single-use portion and includes manually operated buttons configured to control operations of said camera module and is configured to supply image data from said camera module to said computer processing system over said cable;

said second, elongated and rounded proximal part of the single-use portion and said multiple-use portion when mated form a handle of said endoscopic system that has a smooth and rounded outer surface and is configured to be grasped by a hand of a user; and whereby said couplers and an interface between the multiple-use and single-use portions are spaced from the cannula axis, along said handle axis that is transverse to said cannula axis;

a manual rotation control mounted at a proximal side of said multiple-use portion for motion relative to the single-use portion and to said cannula to rotate the cannula around the cannula axis relative to the multiple-use portion;

a first sensor mounted entirely in the multiple-use portion and configured to detect rotational movement or rotational position of the cannula and camera module about the cannula axis relative to the multiple-use portion; and a plural-gear arrangement operationally coupled with said manual control and said first sensor and configured to rotate said cannula and camera module around said cannula axis in response to operation of said manual rotation control and at the same time cause said first sensor to sense rotation of said cannula and camera module around said cannula axis.

2. The endoscopic system of claim 1, further including a second sensor mounted at the multiple-use portion and configured to detect rotational movement or rotational position of the multiple-use portion about an axis parallel to the cannula axis relative to the display monitor.

3. The endoscopic system of claim 2, further including a handheld portion position sensor mounted at said multiple-use portion and configured to detect a position of a selected portion of the handheld portion relative to a selected reference frame.

4. The endoscope system of claim 3, in which said handheld portion position sensor comprises one or more sensors configured to detect a position, in two or more dimensions, of said selected portion of the handheld portion relative to one or more of the processing system, the display, and a patient cavity in which said cannula is inserted.

5. The endoscope system of claim 1, further comprising a horizontal view maintaining circuit coupled with at least one of said first sensor and said computer processing system and configured to maintain an image provided by said camera module and displayed at said display in a selected orientation relative to the display despite rotation of the single-use portion and/or the multiple-use handle portion.

6. The endoscope system of claim 5, wherein said computer processing system can be user-configured to selectively turn off said horizontal view maintaining circuit to thereby allow the orientation of said image on the display to change with rotation of at least one said multiply-use handle portion and said single-use portion.

7. The endoscope system of claim 1, in which said single-use portion comprises a set of at least two single-use portions including one that has a working channel for medical instruments to pass therethrough and is configured for therapeutic use and another that lacks a working channel and is configured for diagnostic use.

8. The endoscope system of claim 1, further including an insert in the cannula of said single-use portion, which insert is bendable by hand and retains a selected bent shape to thereby maintain the cannula in a matching bent shape during a medical procedure using said cannula.

9. The endoscope system of claim 1, further including a surgical drape secured to said single-use portion and a sterile package containing said drape in furled shape and also containing the single-use portion, wherein said surgical drape is configured to unfurl upon opening said surgical package to form a surgical barrier between the multiple-use portion and a patient while said cannula is used in a patient procedure and thereafter to furl around and contain said single-use portion after completion of the procedure.

10. The endoscope system of claim 1, further including a single-use limiter precluding use of the single-use portion in more than one medical procedure.

11. An endoscopic system comprising:

a computer processing system;

a display in electrical communication with the computer processing system for receiving and displaying endoscopic images; and a handheld portion comprising:

a single-use portion that includes (a) an elongated cannula that extends along a cannula axis and has a camera module mounted on a distal end, (b) a first elongated proximal part that also extends along the cannula axis and from which said cannula extends distally, and (c) a second proximal part that extends from said first proximal part in a handle direction that is transverse to the cannula axis and has a distal end spaced a selected distance from said cannula axis in said handle direction;

wherein said cannula is rotatably mounted to said first proximal part to rotate relative thereto about said cannula axis;

a multiple-use portion comprising a rounded housing elongated in said handle direction that has distal and proximal ends and releasably mates at its proximal end with said distal end of the second proximal part of the single-use portion to form therewith a composite, smooth rounded handle that extends in the handle direction transverse to the cannula axis and is configured for a user's hand to grasp the composite handle that comprises both the second proximal part of the single-use portion and the multiple-use portion when mated to form said endoscopic system;

electrical and mechanical couplers at each of the distal end of the second part of the single-use portion and at the proximal end of the multiple-use portion that interlock when the single-use and multiple-use portion are mated;

a manual control at a proximal side of said multiple-use portion configured to be operated by a thumb of a user grasping said handle and coupled with said cannula to selectively rotate the cannula about the cannula axis; and an integrated medical drape secured at the distal end of the second part of the single-use portion and covering the single-use portion before assembly thereof with the multiple-use portion;

said drape being configured to (i) unfurl from the single-use portion after assembly thereof with the multiple use portion (ii) thereafter cover the multiple-use portion loosely and to extend along said handle direction from an interface of the single-use and multiple-use portions while leaving a gap between said handle and the drape for a user's hand to grasp said handle while covered with said drape for a medical procedure, and (c) thereafter again furl over the single use portion to thereby provide a barrier for handling the single-use portion for disposal.

* * * * *